(12) United States Patent  
Götte et al.

(10) Patent No.: US 8,685,030 B2  
(45) Date of Patent: Apr. 1, 2014

(54) PRE-ADJUSTING ADJUSTABLE BONE CUTTING BLOCKS TO ENABLE NAVIGATION OF THE INCISION PLANE WITH RESPECT TO REFERENCE OBJECTS

(75) Inventors: Hubert Götte, München (DE); Jacek Kluzik, Neubiberg (DE)

(73) Assignee: Brainlab AG, Feldkirchen (DE)

( * ) Notice: Subject to any disclaimer, the term of this patent is extended or adjusted under 35 U.S.C. 154(b) by 1415 days.

(21) Appl. No.: 12/147,002

(22) Filed: Jun. 26, 2008

(65) Prior Publication Data

US 2009/0005783 A1  Jan. 1, 2009

Related U.S. Application Data

(60) Provisional application No. 60/951,256, filed on Jul. 23, 2007.

(30) Foreign Application Priority Data

Jun. 26, 2007  (EP) .................................... 07111032

(51) Int. Cl.
*A61B 17/15* (2006.01)
*A61B 17/56* (2006.01)

(52) U.S. Cl.
USPC ................................ 606/87; 606/88; 600/424

(58) Field of Classification Search
USPC ................................ 606/86 R, 87–89, 96–98
See application file for complete search history.

(56) References Cited

U.S. PATENT DOCUMENTS

| | | | |
|---|---|---|---|
| 2006/0161165 A1 * | 7/2006 | Swanson | 606/87 |
| 2006/0195111 A1 * | 8/2006 | Couture | 606/86 |
| 2006/0217733 A1 | 9/2006 | Plassky et al. | |
| 2008/0183176 A1 * | 7/2008 | Canonaco et al. | 606/87 |

FOREIGN PATENT DOCUMENTS

EP    1 690 503 A1    2/2005

* cited by examiner

*Primary Examiner* — Michael T Schaper
(74) *Attorney, Agent, or Firm* — Tucker Ellis LLP

(57) ABSTRACT

The invention relates to a device, system, and method for making an incision into a patient's bone using a cutting block, wherein locations of reference objects of the patient's body are defined with respect to a reference coordinate system. The device may include: a cutting guide having an incision plane; a localization reference for determining a spatial position of the incision plan (the localization reference secured to the cutting guide); a fixation device secured to the bone; an adjusting device for setting a position of the incision plane relative to the bone, wherein a location of the adjusting device is defined with respect to a base coordinate system; and a pre-adjusting device for aligning the base coordinate system with respect to the reference coordinate system.

7 Claims, 9 Drawing Sheets

PRE-ADJUSTING ADJUSTABLE BONE CUTTING BLOCKS TO ENABLE NAVIGATION OF THE INCISION PLANE WITH RESPECT TO REFERENCE OBJECTS

RELATED APPLICATION DATA

This application claims priority of U.S. Provisional Application No. 60/951,256 filed on Jul. 23, 2007, and EP 07111032 filed on Jun. 26, 2007, which are incorporated herein by reference in their entirety.

FIELD OF THE INVENTION

The invention relates to an adjustable cutting block that can be pre-adjusted to enable medical navigation with respect to reference objects of a patient's body when setting an incision plane (defined by the location of its cutting guide). The invention also relates to a system and a method for medically navigating the incision plane of the cutting guide of the cutting block with respect to reference objects of a patient's body.

BACKGROUND OF THE INVENTION

In computer-assisted knee arthroplasty, a cutting block is commonly used that includes a cutting guide to which a localization reference, such as an infrared radiation emitting or reflecting reference star, is attached. The localization reference can be spatially adjusted (for example, rotated) to allow a medical navigation system to have a good view of the reference. Using the localization reference and the medical navigation system, the cutting block may be positioned such that the cutting guide is located in a planned incision plane.

EP 1 690 503 A1 discloses a bone cutting block that includes: a cutting guide to which a localization reference is adjustably attached that allows the incision plane of the cutting guide to be spatially determined; a fixation device that can be fixed to a bone; an adjusting device between the fixation device and the cutting guide, wherein the incision plane of the cutting guide relative to the bone can be set using the adjusting device, wherein the spatial location of the adjusting device can be determined using a registration element. EP 1 690 503 A1 is incorporated by reference herein in its entirety.

Such adjusting devices may include setting elements such as hand wheel screw setting elements. Using the setting elements, the cutting guide can be rotated about at least two non-parallel axes and adjusted in height, wherein each setting element may change one mechanical degree of freedom of the cutting guide. The change in a mechanical degree of freedom of the cutting guide leads to a change in the corresponding degree of freedom of the incision plane with respect to a bone coordinate system (with respect to which the cutting guide or the incision plane of the cutting guide is defined). Such a conventional cutting block enables navigation with respect to a predetermined navigation plan. In the navigation plan, an incision plane may be set or aligned to a predetermined spatial location of a target incision plane using a medical navigation system.

Use of a conventional cutting block requires a time-consuming number of iterations by repeatedly adjusting the setting elements. In so-called "navigation-to-reference," the incision plane is aligned in a reference coordinate system determined by defined projection planes. The projection planes can be defined with respect to pre-operatively determined references such as characteristic planes or axes or points of a body. The reason that a number of iterations are required is that changes made to a setting element of the adjusting device not only cause a change in the desired degree of freedom of the incision plane in the reference coordinate system, but additionally changes at least one other degree of freedom of the incision plane relative to the references. If, for example, particular distances of the incision plane of the cutting block relative to planes or axes or points of the body are to be maintained, and if a first distance has been set by repeatedly adjusting the setting elements, the attempt to set a second distance of the incision plane or cutting guide relative to another axis or plane or point by changing the respective setting element will also adjust the first distance. Therefore, a large number of iterations are often required to precisely set the incision plane with respect to the references in the reference coordinate system.

Navigation with respect to references or reference objects of a body means that the incision plane of a cutting guide can be set in a reference coordinate system with respect to characteristic (or pre-operatively or intra-operatively determined or selected) reference objects of a body. Such reference objects of the body may include:

characteristic planes (for example, the tibial plateau, the sagittal plane, the frontal plane or the transversal plane);
axes (for example, the femoral axis or the tibial axis); or
points of a body (for example, the attachments of the cruciate ligaments).

The incision plane can be set such that it maintains specified distances from the planes, axes, or points of the body that are predetermined by the surgeon.

This method of navigation ordinarily benefits from the experience of the surgeon, who knows the distances that the cutting guide or the incision plane of the cutting guide should maintain relative to the selected references for the cutting guide to be properly placed. Some surgeons prefer to navigate with respect to reference objects, since the distances from the reference objects that are desired can be directly set. Additionally, navigation with respect to reference objects eliminates the need for a navigation planning step.

SUMMARY OF THE INVENTION

A cutting block for making an incision into a patient's bone in accordance with the invention may include one or more of the following.

A reference coordinate system defined with respect to locations of reference objects of the patient's body.

A cutting guide having an incision plane.

A localization reference secured to the cutting guide for determining a spatial position of the incision plane.

A fixation device secured to the bone.

An adjusting device for setting a position of the incision plane relative to the bone, wherein a location of the adjusting device is defined with respect to a base coordinate system.

A pre-adjusting device for aligning the base coordinate system with respect to the reference coordinate system.

The reference coordinate system may be formed by two image planes that are perpendicular to each other, such as the frontal plane or sagittal plane of a patient's body or a part of a patient's body. The incision plane or position and/or orientation of the incision plane or cutting guide (ascertained using the navigation system via the localization reference) is defined with respect to the bone coordinate system. Accordingly, the spatial location of the incision plane (or the spatial position and/or orientation of the incision plane or cutting guide) with respect to the bone coordinate system is known to the navigation system. If the reference objects or the positions and/or orientations of the reference objects are selected with respect to the bone coordinate system, then the locations of the reference objects with respect to the bone coordinate system are known to the navigation system. If the reference objects are defined with respect to the reference coordinate system, or if the reference coordinate system is formed by the reference objects, then a transformation matrix between the bone coordinate system and the reference coordinate system can be ascertained by the navigation system. Accordingly, the bone coordinate system can be transformed into the reference coordinate system and, conversely, the reference coordinate system can be transformed into the bone coordinate system. The locations of the incision plane and reference objects can thus be ascertained and displayed in the reference coordinate system, and the location of the incision plane and the reference objects can be ascertained and displayed in the bone coordinate system.

In the prior art, since the rotational axes of the reference coordinate system (and of the mechanism of the cutting block or the adjusting device) are generally different, changing one setting element arranged on the adjusting device (to set a direction or mechanical degree of freedom of the cutting guide with respect to the reference coordinate system) also generally leads to changes in the incision plane in more than one degree of freedom (or in degrees of freedom other than that intended to be changed using the setting element). Accordingly, adjusting one degree of freedom (for example, to set a desired distance with respect to a reference) often causes an undesired change in another degree of freedom. This undesired adjustment relationship may lead to significant difficulties in aligning the incision plane with respect to the references or reference objects in the reference coordinate system and may necessitate a readjustment in a large number of steps. Hence, effective navigation using prior art cutting blocks with respect to references may not be possible or may only be possible in a way that is too time-consuming for practical applications.

The cutting block in accordance with the invention includes a pre-adjusting device for pre-aligning a base coordinate system with respect to the reference coordinate system. The pre-adjusting device may include a single pre-adjusting setting element or one individual setting element for each respective degree of freedom. An exemplary device may include two hand wheel setting screws or locking screws for aligning the base coordinate system with respect to the reference coordinate system. The pre-adjusting device may include joints, such as ball joints or at least two hinged joints, about which the device can be rotated or aligned. During the pre-adjusting procedure, a reference star may be assigned to the base coordinate system of the cutting block or to the cutting block, such that the alignment of the base coordinate system can be determined using a navigation system.

Pre-adjustment using the pre-adjusting device in accordance with the invention may be performed until the base coordinate system is almost aligned or has been aligned with respect to the reference coordinate system. Almost aligning in the sense of the invention is not necessarily understood to mean that the base coordinate system, once aligned, lies exactly on the reference coordinate system or that all of the axes of the base coordinate system must lie parallel to the axes of the reference coordinate system. Pre-adjusting is complete once a first axis of the base coordinate system runs almost parallel (e.g., to within ±1 degree) to a plane spanned by two axes of the reference coordinate system, and a second axis of the base coordinate system runs almost parallel (e.g., to within ±1 degree) to the third axis of the reference coordinate system. After such an alignment has been performed, two axes of the base coordinate system can run non-parallel to the corresponding axes of the reference coordinate system. Even then, the base coordinate system is, in accordance with the invention, "almost aligned" with respect to the reference coordinate system. In accordance with the invention, however, the reference coordinate system and the base coordinate system can also be exactly aligned relative to each other.

Once the base coordinate system has been aligned with respect to the reference coordinate system, advantages of the invention become clear. If the base coordinate system is almost aligned to the reference coordinate system, one may use a navigation system to quickly determine the incision plane with respect to the reference coordinate system or with respect to the reference objects of the body in the reference coordinate system. It is thus possible to perform navigation with respect to the references or reference objects in a small number of steps or iterations. The changes or movements to the cutting guide made by setting the setting elements of the adjusting device can be at least partly ascertained and displayed as mutually decoupled changes in the degrees of freedom of the incision plane with respect to the references in the reference coordinate system. Thus, changing a mechanical degree of freedom of the cutting guide on the adjusting device only causes a change in the same degree of freedom of the incision plane in the reference coordinate system.

By "almost" setting the first degree of freedom of the incision plane, then changing a second mechanical degree of freedom of the cutting guide only causes a change in the second corresponding degree of freedom of the incision plane in the reference coordinate system, without the first degree of freedom of the incision plane also being changed. The setting elements of the adjusting device can then be set in a small number of steps, such that the incision plane maintains distances that are predetermined or specified by the surgeon in the reference coordinate system with respect to particular planes or axes or points of the body. The incision plane or a projection of the incision plane forms angles with characteristic axes and/or planes of a body (such as the varus/valgus angle or the flexion/extension angle) that maintain particular predetermined angular values. This alignment enables the incision plane of the cutting guide to be quickly navigated relative to references in a small number of iterations.

Since the base coordinate system is aligned with respect to the reference coordinate system, it is possible (once a first degree of freedom of the incision plane of the cutting guide has been set by changing a first setting element of the adjusting device) to change the incision plane in one degree of freedom only in the reference coordinate system by changing another setting element of the adjusting device. This single degree of freedom adjustment prevents the setting of one setting element of the adjusting device from influencing (or partly reversing the setting of another setting element) in the reference coordinate system. A first degree of freedom of the incision plane, such as a first rotation, can be changed or set using a first setting element (for example, a first hand wheel setting screw) until the navigation system indicates that the desired distance or angular value relative to a reference has been reached. Given this setting, at least one degree of freedom of the incision plane is still not decoupled from the first degree of freedom of the incision plane that is set by the first setting element. Once the first degree of freedom has been set, a second degree of freedom of the incision plane, (such as another rotational degree of freedom) can be changed by a user using a second setting element, without changing the first degree of freedom. It is thus possible to specifically set a second distance value or angular value relative to a reference.

Changing a third degree of freedom (for example, a translational degree of freedom) also does not change the first and second degree of freedom of the incision plane or the first and second distance or angular value set in the reference coordinate system. When using three setting elements, it is possible to set the cutting guide or the incision plane of the cutting guide with respect to the references in three setting steps.

The pre-adjusting device may be formed between the fixation device of the cutting block and the adjusting device and preferably comprises joints (for example, ball joints or at least two hinges) about which the base coordinate system can be moved or rotated.

A system in accordance with the invention allows navigating the cutting guide of the cutting block with respect to references of a patient's body. Using such a system, it is possible to prepare or set the cutting block such that it can be used for quickly navigating with respect to reference objects of the patient's body. Once the preparation of the cutting block is complete, it is possible to navigate the cutting guide or the incision plane of the cutting block with respect to reference objects or references such as planes, axes (for example, the femoral axis or the tibial axis) or points of a body. The system includes a navigation system having a computational unit (for example, a computer or processor) that is in communication with the navigation system by wired connection, wirelessly, or is integrated into the navigation system. Using a sensor array (for example, infrared cameras) the navigation system can detect localization references, such as infrared radiation reflecting or emitting reference stars, or registration elements that are arranged on the cutting guide and at least temporarily on the adjusting device of the cutting block. The computational unit can ascertain the location or the positions and/or orientations of: the incision plane of the cutting guide, the adjusting device, and the pre-adjusting device, with respect to the bone, from the detected localization references. The absolute locations of: the incision plane, the adjusting device, and the pre-adjusting device and the locations of: the incision plane, the adjusting device, and the pre-adjusting device relative to each other are thus known to the navigation system.

The bone coordinate system is known to the navigation system or can be ascertained by the navigation system, wherein the position and/or orientation of the cutting guide of the incision plane of the cutting guide may be defined with respect to the bone coordinate system. The position and/or orientation of the incision plane can also be ascertained in the reference coordinate system.

The reference coordinate system is also known to the navigation system or can be ascertained by the navigation system, wherein the position and/or orientation of reference objects of the body, such as reference points, reference axes, reference straight lines or reference planes, can be defined with respect to the reference coordinate system. The reference coordinate system may be situated on or in the patient's body (for example, on the bone on which the cutting block is arranged), and can be determined or formed by projection planes such as the frontal plane or the sagittal plane.

The base coordinate system can be freely selectable or can be situated between the pre-adjusting device and the adjusting device (for example, at their connecting point). The base coordinate system can be almost aligned relative to the reference coordinate system using the pre-adjusting device (for example, by adjusting the setting elements of the pre-adjusting device). If the base coordinate system and the reference coordinate system are not almost aligned with respect to each other, then adjusting a setting element of the adjusting device (that is provided for changing a mechanical degree of freedom of the cutting guide relative to the base coordinate system) not only changes the desired degree of freedom of the cutting guide or the incision plane of the cutting block relative to the reference coordinate system, but also changes at least one additional degree of freedom of the incision plane.

Once the base coordinate system is or has been almost aligned with respect to the reference coordinate system by setting or changing the setting element of the pre-adjusting device, adjusting a setting element that serves to change a mechanical degree of freedom of the cutting guide in the reference coordinate system also partly changes the incision plane in one degree of freedom only relative to the references.

To set the degrees of freedom as desired, the computational unit determines the location or the position and/or orientation of the incision plane of the cutting guide relative to the positions and/or orientations of the reference objects that are known to the computational unit or ascertained by the computational unit. The relative location or relative distance between the incision plane and the reference objects may be determined by the computational unit and may be displayed or outputted on a display device such as a monitor or screen. Numerical values can be provided be the computational unit that symbolize the distances between the incision plane and the respective references, and from which the surgeon can tell whether the desired distances between the incision plane and the reference objects have been reached, or by how much the actual distances deviate from the desired distances. The position and/or orientation of the incision plane relative to the reference objects can also be graphically or schematically displayed on the display device. By adjusting the setting element of the adjusting device, the surgeon can specifically adjust every other degree of freedom of the incision plane relative to the reference coordinate system. The surgeon can do this independently or decoupled from other degrees of freedom, until the desired distances between the incision plane and the reference objects are set or provided. It is also possible, once the first degree of freedom has been set, to use each setting element of the adjusting device to adjust a single degree of freedom of the incision plane, decoupled from the other degrees of freedom, relative to the references or in the reference coordinate system.

The invention also relates to a method for navigating a cutting guide of the cutting block with respect to reference objects of a patient's body, wherein localization references or registration elements that are arranged on the cutting guide (and at least temporarily on the adjusting device) are detected and tracked using a navigation system. The navigation system may include infrared cameras, and the location or the position and/or orientation of the incision plane of the cutting guide and the adjusting device may be ascertained with respect to a bone coordinate system using a computational unit that is connected to or integrated into the navigation system. A base coordinate system (with respect to which the location of the adjusting device is defined) can be adjusted or changed translationally or rotationally, using setting elements arranged on the pre-adjusting device. The base coordinate system is moved until it is almost aligned with respect to a reference coordinate system with respect to which the position and/or orientation of reference objects of the body is defined. The reference objects can be selected in the bone coordinate system such that the bone coordinate system and the reference coordinate system can be mutually transformed.

Once the base coordinate system has been aligned or pre-adjusted relative to the reference coordinate system, the localization reference may be removed from the adjusting device.

In other words, the localization reference may be arranged on the adjusting device until the aligning or pre-adjusting procedure is complete.

After aligning or pre-adjusting, the computational unit may also ascertain the position and/or orientation of the incision plane of the cutting guide relative to the positions and/or orientations of the reference objects that are known to the computational unit or ascertained by the computational unit. The ascertained positions or distances of the incision plane relative to the reference objects or between the incision plane and the reference objects may be provided or displayed, such that (based on the ascertained position and/or orientation of the incision plane relative to the reference objects) the surgeon may change the position and/or orientation of the incision plane with respect to the reference objects by changing the adjusting device, until the cutting guide or the incision plane is positioned at predetermined distances from the reference objects.

The pre-adjusting device may align or pre-adjust the base coordinate system with respect to the reference coordinate system such that a first axis of the base coordinate system runs almost parallel to a plane spanned by two axes of the reference coordinate system, and a second axis of the base coordinate system runs almost parallel to another of the axes or to the third axis of the reference coordinate system.

Once the base coordinate system has been aligned or pre-adjusted with respect to the reference coordinate system, the cutting guide or the incision plane can be changed in only one degree of freedom relative to the reference coordinate system by changing a setting element of the adjusting device. In other words, the cutting guide or the incision plane can be moved with respect to the reference coordinate system in mutually decoupled degrees of freedom, such that it is possible to quickly align the incision plane relative to the reference objects.

The invention also relates to a computer program that, when it is loaded onto a computer or is running on a computer, performs the method in accordance with the invention, and to a program storage medium or computer program product for executing the program.

BRIEF DESCRIPTION OF THE DRAWINGS

The forgoing and other features of the invention are hereinafter discussed with reference to the figures.

DETAILED DESCRIPTION

Figure 1:
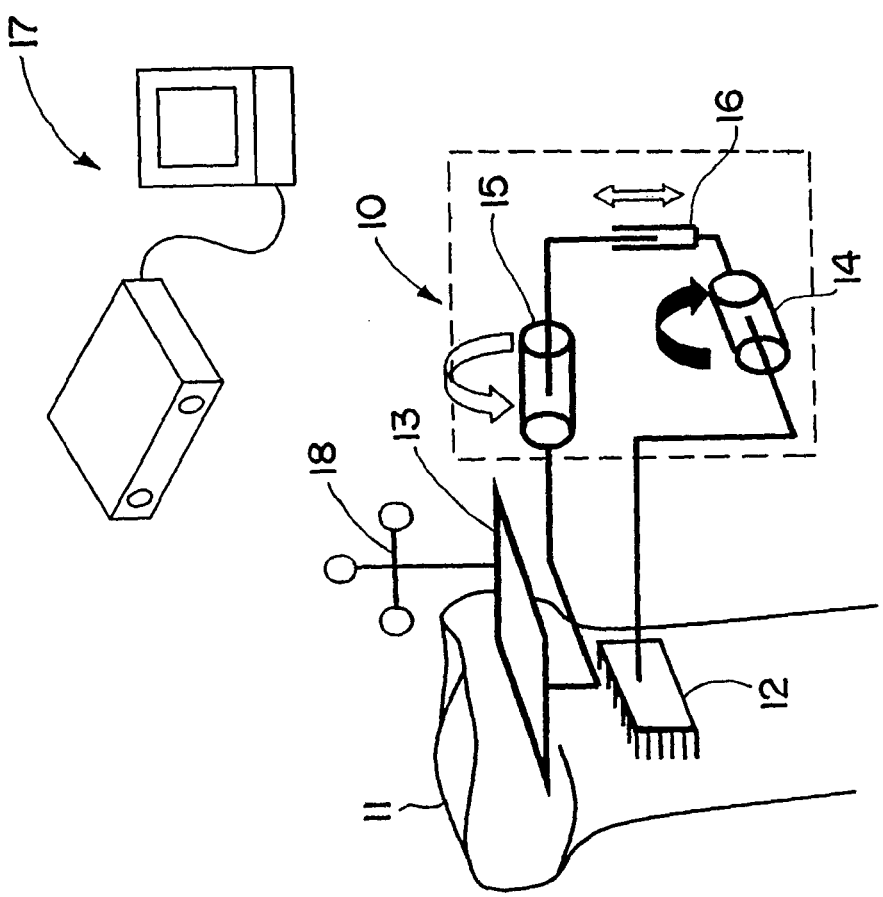
FIG. 1 illustrates an adjusting device of a conventional cutting block.

FIG. 1 shows an adjusting device 10 of a conventional prior art cutting block. The cutting block is arranged on a bone 11 via a fixation device 12. The adjusting device 10 is arranged between a cutting guide 13 and the fixation device 12 and comprises three joints 14, 15, 16. The joints 14, 15, 16 are connected to a setting element of the cutting block, such as hand wheel setting screws, such that setting a setting element causes a movement of the corresponding or assigned joint of the joints 14, 15, 16. By moving the setting element and therefore the joints 14, 15, 16, it is possible to correspondingly move the cutting guide 13, such that the position and/or orientation or location of the cutting guide 13 is changed. Rotational movements can be performed via the two joints 14, 15, such that the cutting guide 13 is rotated in accordance with the change in the setting element and therefore the joints 14, 15. Translational movements can be transferred from the setting means onto the cutting guide 13 via the joint 16, such that the cutting guide 13 can perform translational movements. The position of the cutting guide 13, for example, can be monitored by a medical navigation system 17 with the aid of an infrared radiation emitting or reflecting reference star 18 or other localization reference or other registration element that is arranged on the cutting guide 13. By changing the setting element, it is possible to align the cutting guide 13 such that the incision plane through the bone 11 that actually results in this position of the cutting guide 13 corresponds to a target incision plane or planning incision plane that is planned or, for example, predetermined by a surgeon. The incision plane and the target incision plane can be defined in the navigation system 17 with respect to a base coordinate system that is connected to the adjusting device 10, such that the location of the incision plane and the target incision plane is known with respect to the base coordinate system, and changes in the location of the incision plane and the target incision plane can be ascertained and monitored. If, however, no such attempt is made to navigate the incision plane with respect to a predetermined plan (for example, to align it to the target incision plane or with respect to the target incision plane) but instead to align or navigate the incision plane with respect to references or reference objects in the bone 11 that are defined in a reference coordinate system, then the navigation procedure using the conventional cutting block becomes difficult and slow. For if the position and/or orientation of the cutting guide 13 of the cutting block is moved or changed in one degree of freedom, the position of the incision plane is changed, with respect to the reference coordinate system that is virtually placed in or on the bone 11 and with respect to which the references are defined, in at least one degree of freedom other than the desired degree of freedom, since the rotational axes of the mechanism of the adjusting device 10 and of the reference coordinate system are different and not aligned to each other. Unintentional changes or adjustments to the incision plane with respect to the reference coordinate system should be corrected, wherein each of the correction movements of a setting element not only causes a movement of the incision plane in the desired degree of freedom but also in at least one other, undesired degree of freedom. Thus, using a conventional cutting block, navigation with respect to references is only possible with repeated iterations that are not practical due to the time required to make the iterations.

Figure 2:
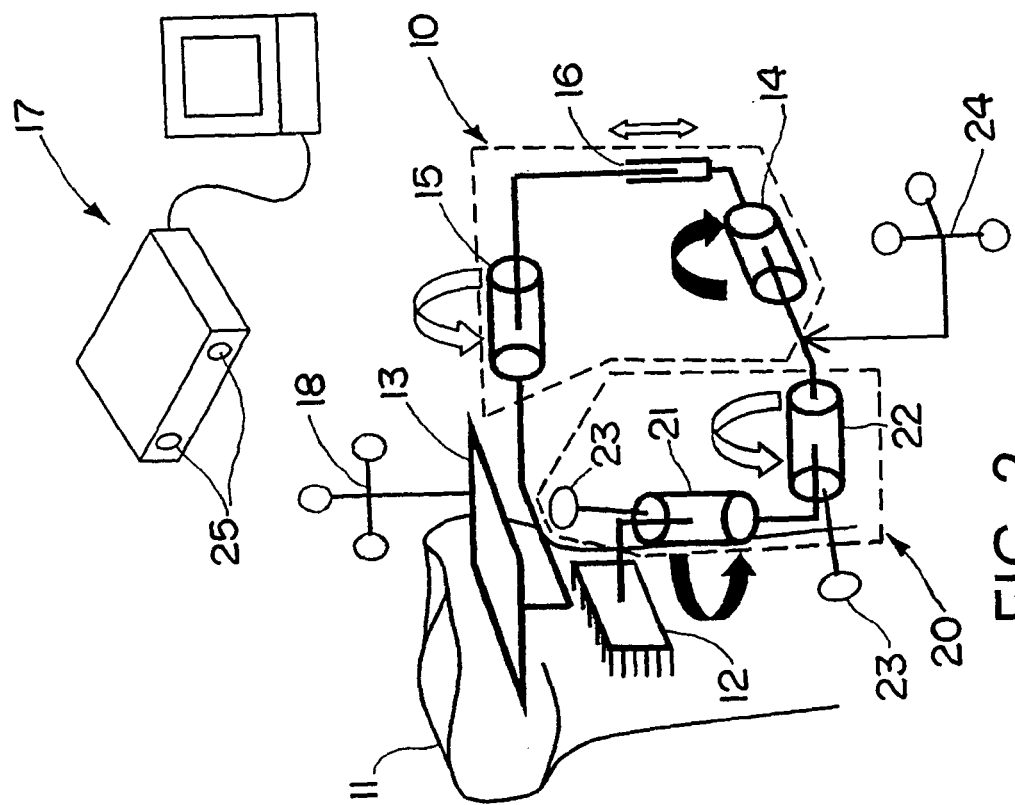
FIG. 2 illustrates an adjusting device and a pre-adjusting device in accordance with an exemplary embodiment of the invention.

FIG. 2 illustrates an exemplary embodiment of a pre-adjusting device 20 of a cutting block. As explained with respect to FIG. 1, the cutting block is attached to a bone 11 via a fixation device 12. In addition to the adjusting device 10 comprising three joints 14, 15, 16, a pre-adjusting device 20 is arranged on the cutting block between the adjusting device 10 and the fixation device 12. The pre-adjusting device 20 includes, for example, a ball joint, depicted by two hinged joints 21, 22, via which rotational movements can be transferred. A setting element, for example, a hand wheel setting screw 23, of the pre-adjusting device 20 is connected to each of the joints 21, 22 respectively and can be adjusted and rotated by a user, such that changing a setting element causes a rotation or movement about whichever one of the joints 21, 22 to which the setting element is connected. The position and/or orientation of the adjusting device 10 and of the pre-adjusting device 20 can be ascertained by a medical navigation system 17, such that the location of the adjusting device 10 and of the pre-adjusting device 20 is known to the navigation system 17. For example, the navigation system 17 can detect a position of a reference star 24 or other registration element arranged on the adjusting device 10 and the pre-adjusting device 20 by means of infrared cameras 25.

Figure 3:
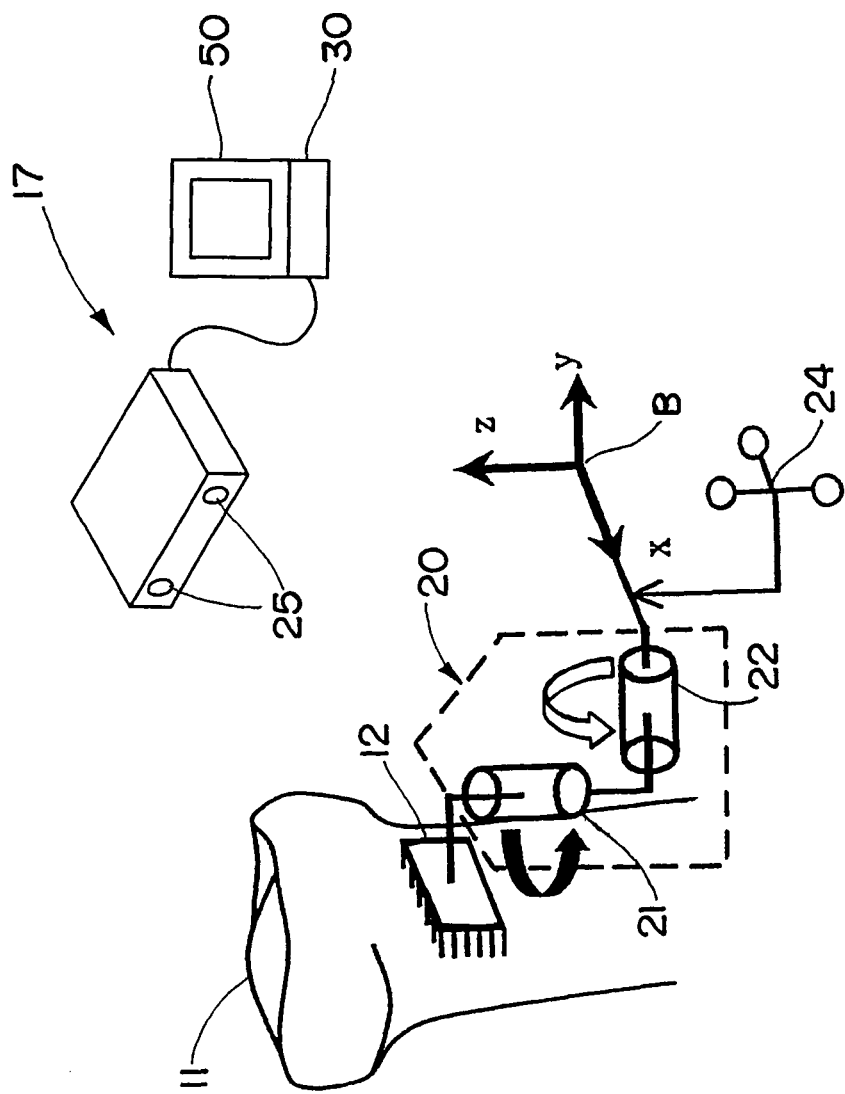
FIG. 3 illustrates the pre-adjusting device of FIG. 2, in use during an exemplary pre-adjusting procedure.

Turning to FIG. 3, a computational unit 30 of the navigation system 17 can virtually define or select a base coordinate system B that is connected to the pre-adjusting device 20 such that a rotation of one of the joints 21, 22 causes a rotation of the base coordinate system B. The reference star 24 may be arranged on the pre-adjusting device 20 until the base coordinate system B has been rotated or aligned as desired. The reference star 24 then may be optionally removed from the pre-adjusting device 20.

The base coordinate system B may be moved or rotated about the corresponding joints 21, 22 using the setting element 23 of the pre-adjusting device 20 until the base coordinate system B is aligned relative to a reference coordinate system R. The reference coordinate system R may be defined by the navigation system 17 on or in the bone 11 and with respect to which references or reference objects of the bone 11 or of a patient's body can be defined.

Figure 4C:
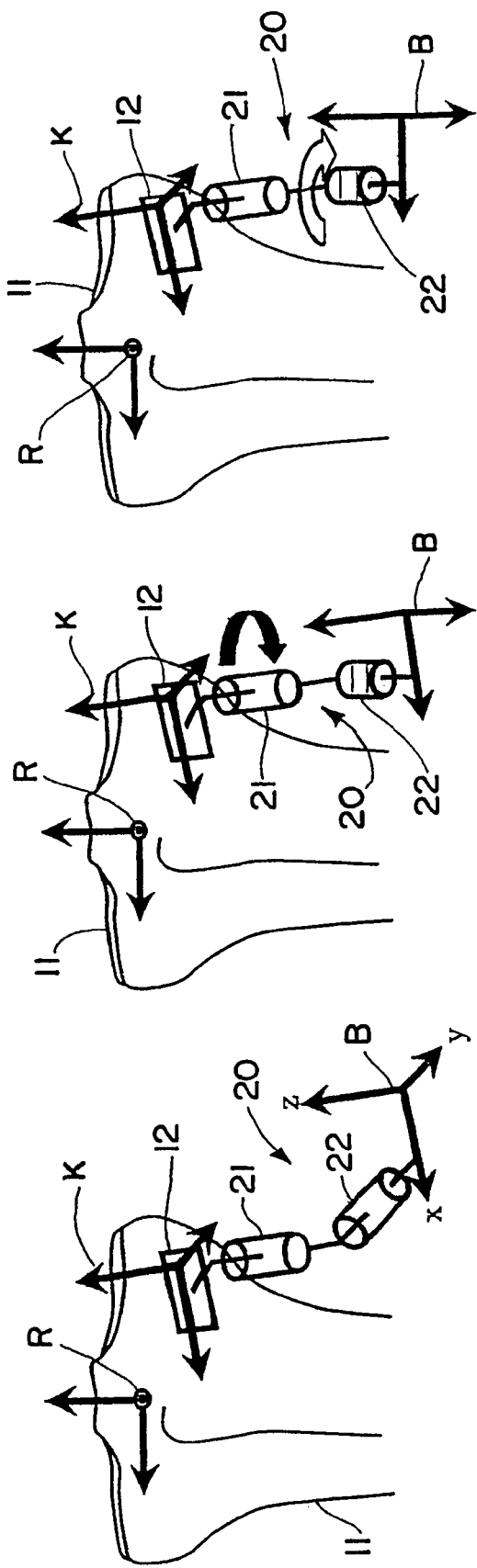
FIGS. 4a-4c illustrate a procedure for aligning a base coordinate system B to a reference coordinate system R, during an exemplary pre-adjusting procedure.
Figure 4C:
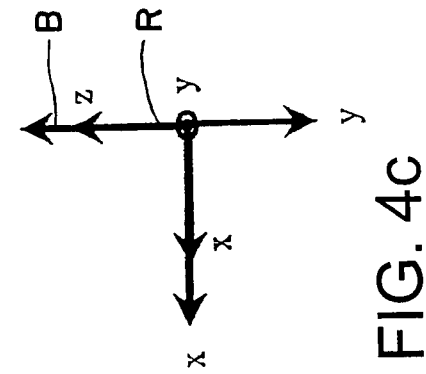
Figure 4B:
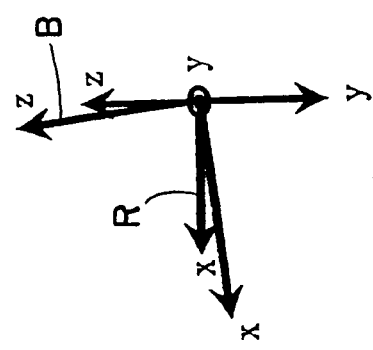
Figure 4A:
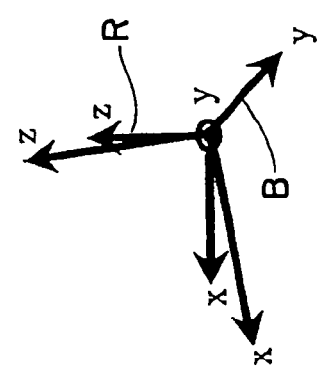

Turning to FIGS. 4a-4c, initially, the base coordinate system B and reference coordinate system R are not aligned to each other, as shown in FIG. 4a.

By rotating the setting element connected to the joint 21, the base coordinate system B is rotated about the joint 21 until it is possible to tell, with the aid of the navigation system, that the y-axis of the base coordinate system B is lying in the y-z plane of the reference coordinate system R (see FIG. 4b). Alternatively, it is also possible to rotate the x-axis of the base coordinate system B into the x-y plane of the reference coordinate system R or to rotate the z-axis of the base coordinate system B into the x-z plane of the reference coordinate system R. In a subsequent step, the setting element of the pre-adjusting device 20 that is connected to the joint 22 may be rotated until it is possible to determine, with the aid of the navigation system, that the x-axis of the base coordinate system B is lying on the x-axis of the reference coordinate system R (see FIG. 4c). If the other possible alignments were previously selected, it is alternatively possible in this step to rotate the z-axis of the base coordinate system B onto the z-axis of the reference coordinate system R or to rotate the y-axis of the base coordinate system B onto the y-axis of the reference coordinate system R. Alignment is complete when the x-axis of the base coordinate system B is lying on the x-axis of the reference coordinate system R and the y-axis of the base coordinate system B is lying in the y-z plane of the reference coordinate system R, as shown in FIG. 4c. Alignment may be completed in as few as two steps, by rotating about the joints 21, 22. In FIGS. 4a to 4c, the bone coordinate system K is defined with respect to the fixation device 12 of the cutting block. The bone coordinate system K, however, can be assigned to another position on the bone. The location of the bone coordinate system K may be fixed or defined before the cutting block is attached to or arranged on the bone 11.

Figure 5B:
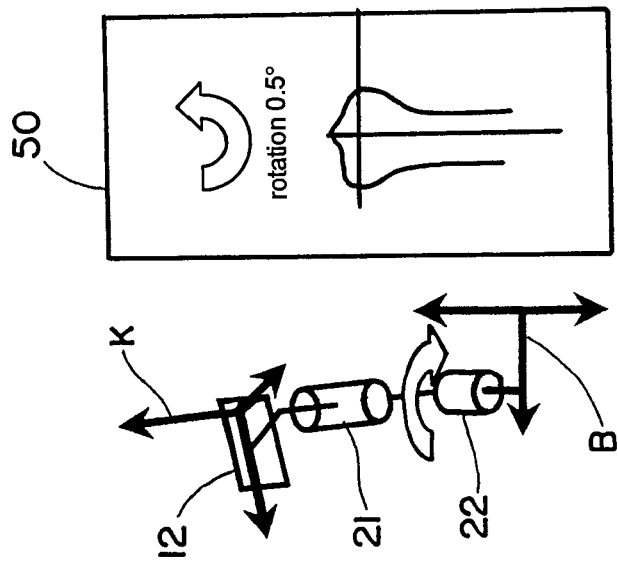
FIGS. 5a-5b illustrate an exemplary procedure for aligning two axes of the base coordinate system B using two joints of an exemplary pre-adjusting device.
Figure 5A:
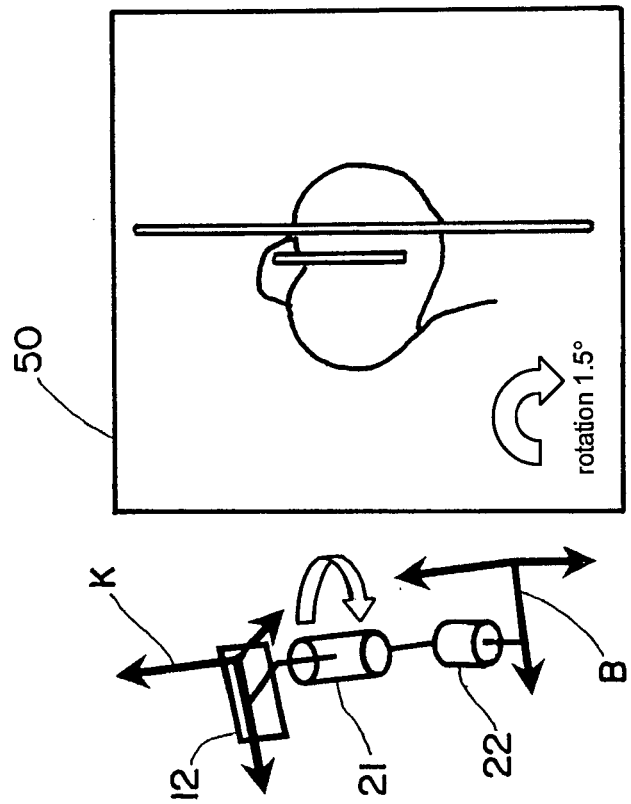

FIGS. 5a and 5b show how the alignment of two axes of the base coordinate system B, using the two joints 21, 22 of the pre-adjusting device 20, can be displayed or visualized on the navigation system, for example, by a representation of the bone and of the two axes of the base coordinate system B that are indicated or displayed on a screen 50. FIGS. 5a and 5b also show a bone coordinate system K with respect to which the location of the fixation device 12 is defined.

Figure 6B:
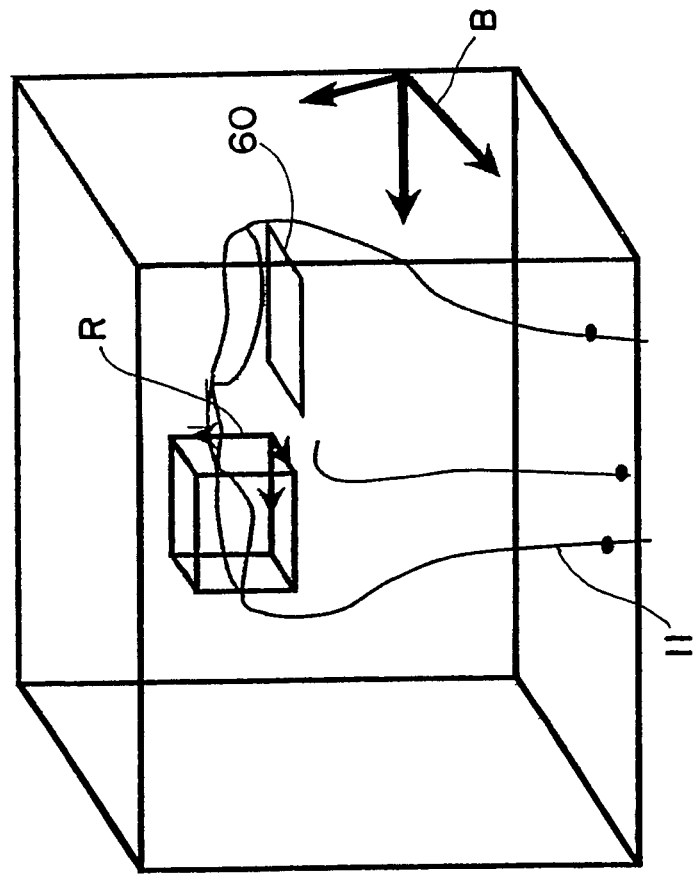
FIGS. 6a-6e illustrate a procedure for navigating an incision plane of the cutting block with respect to references of a body in accordance with an exemplary embodiment of the invention.
Figure 6A:
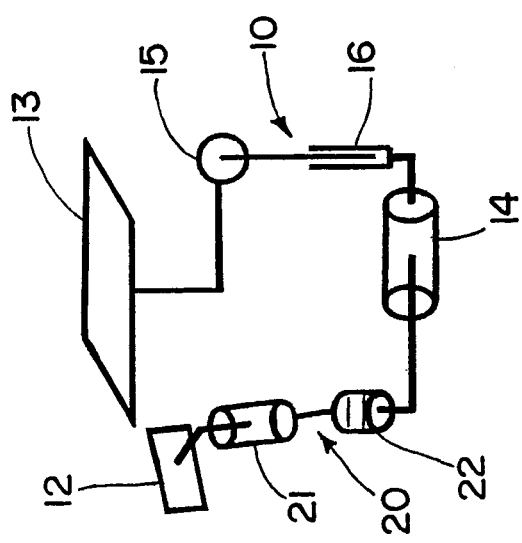
Figure 6D:
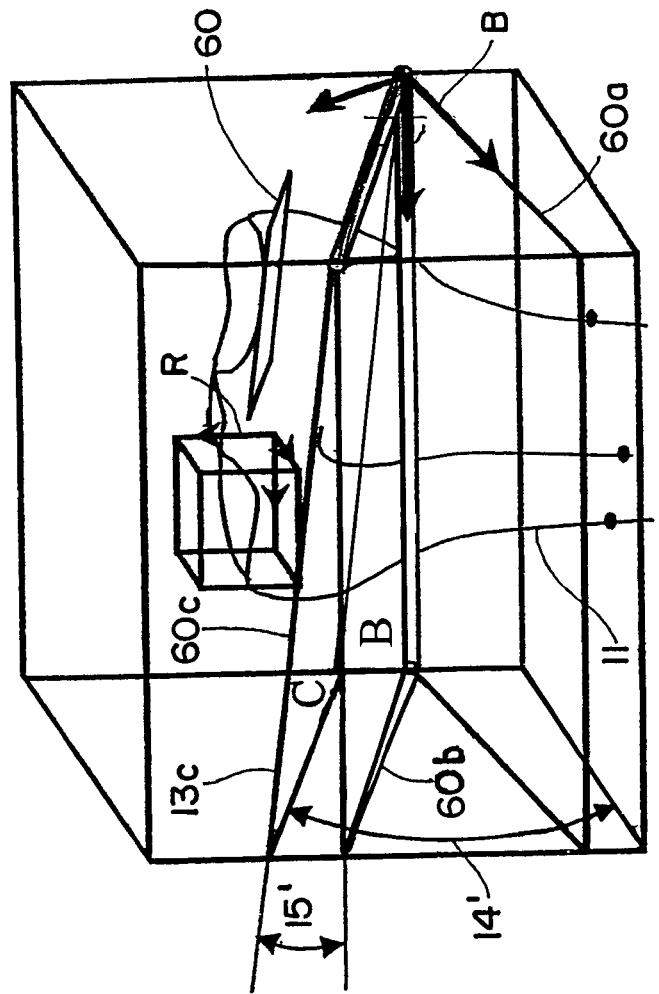
Figure 6C:
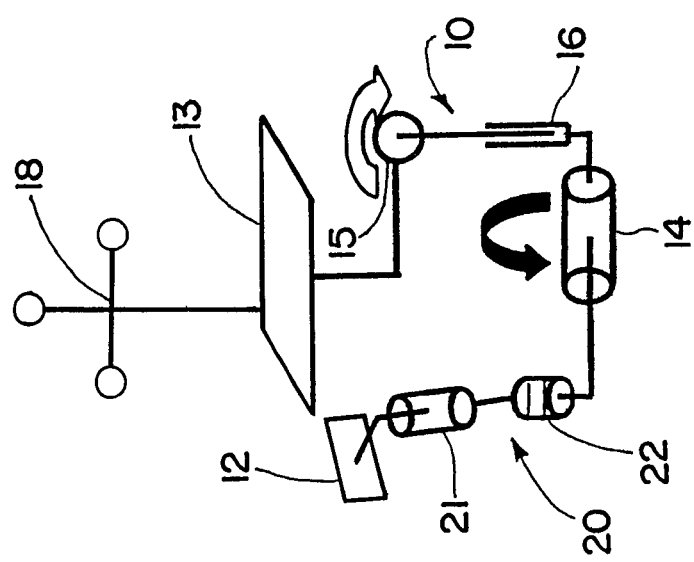

Turning now to FIGS. 6a through 6e, once the base coordinate system B has been aligned to the reference coordinate system R (as shown in FIG. 6b) the cutting guide 13 and therefore the incision plane 60 of the cutting block can be set. (The incision plane 60 can have any initial location as shown in FIG. 6b or FIG. 6d) The cutting guide 13 and the incision plane 60 can be set with respect to reference objects using the adjusting device 10, by adjusting the setting elements connected to the joints 14, 15, 16 (see FIG. 6a). The location of the incision plane 60 can be ascertained using the navigation system, with the aid of the localization reference 18 (for example, a reference star) that may be arranged on the cutting guide 13.

Turning to FIG. 6d, the navigation system first ascertains the initial location of the incision plane 60, in particular relative to the bone 11, and, for example, displays it on a monitor or screen. The incision plane 60 is situated in its initial location 60a in FIG. 6d. By adjusting the setting element connected to the joint 14 of the adjusting device 10, the incision plane 60 is rotated from the position 60a into the position 60b, such that the flexion/extension desired or predetermined by a surgeon is set. By adjusting the setting element connected to the joint 15, the incision plane 60 is moved from the position 60b into the position 60c, until the predetermined varus/valgus angle is reached. Lastly, by setting the setting element connected to the joint 16, the predetermined resection is set. During these settings, the navigation system assists the surgeon by ascertaining, monitoring and displaying the change in the flexion/extension, the varus/valgus angle and the resection, while the setting elements are being adjusted, such that the surgeon can quickly set the desired values.

Figure 6E:
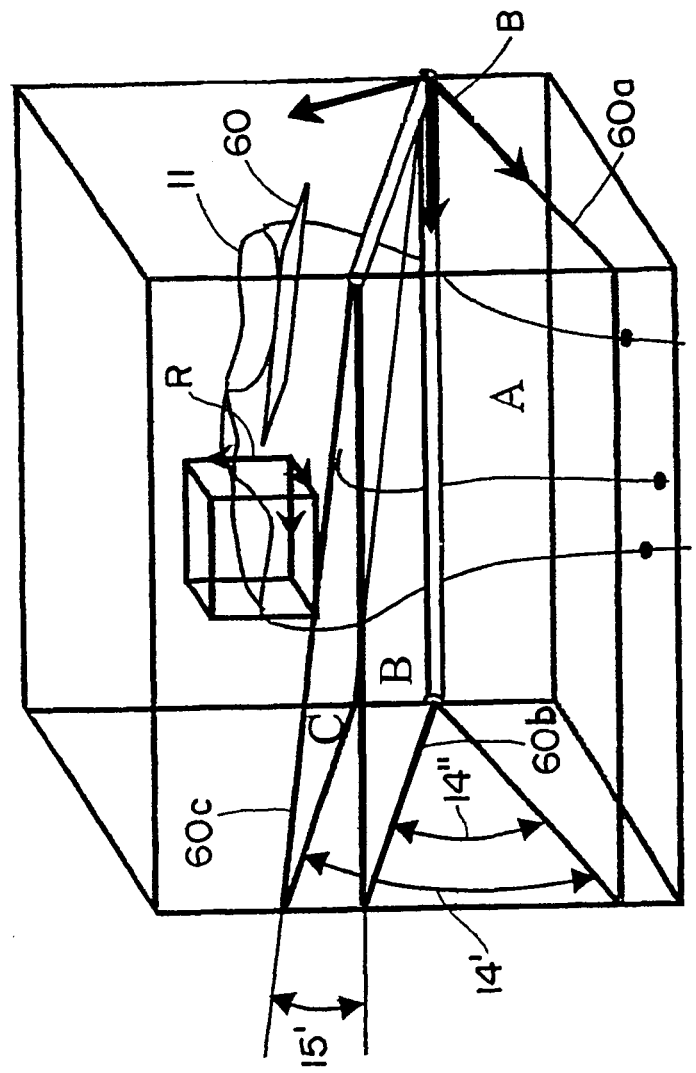

Turning to FIG. 6e, the desired flexion angle is set first by adjusting the setting element connected to the joint 14. Since the base coordinate system B has been almost aligned with respect to the reference coordinate system R, when the varus angle is changed using the setting element connected to the joint 15, the flexion angle 14 before the varus angle is set and the flexion angle 14' after the varus angle is set remain the same (see FIG. 6e). It is thus possible to change the degrees of freedom of the incision plane 60, mutually decoupled, in the reference coordinate system R.

Figure 7:
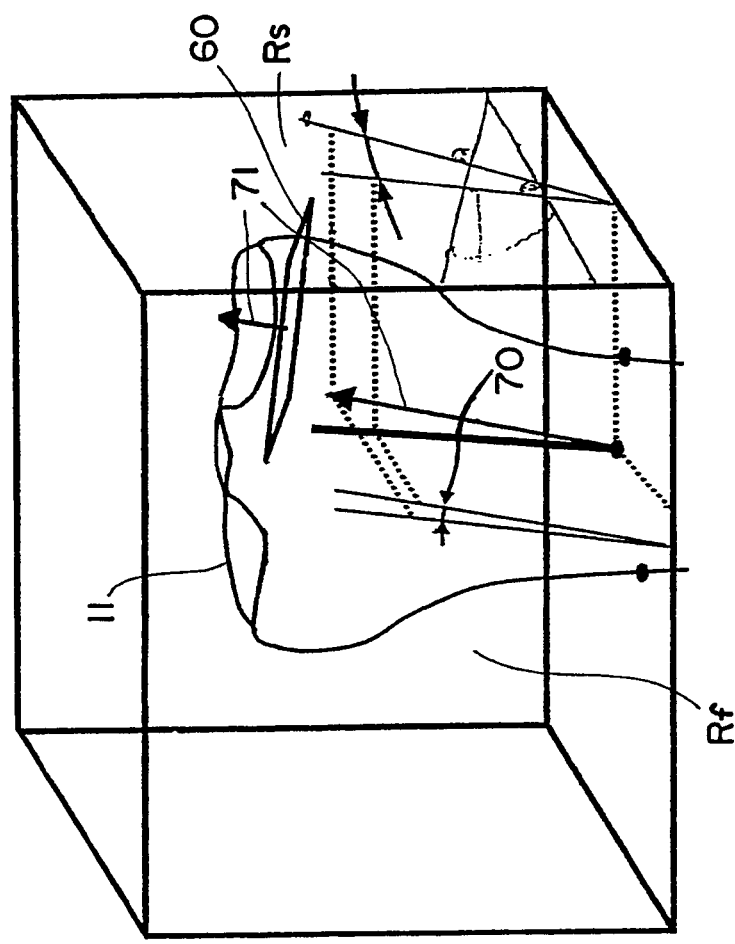
FIG. 7 illustrates determining the position of an incision plane with respect to the references.

Turning to FIG. 7, to set the flexion/extension angle and the varus/valgus angle, the angles between an axis 70 that serves as a reference and the incision normal 71 of the incision plane are projected onto the sagittal plane Rs and the frontal plane Rf that span the reference coordinate system R, and set as desired or as specified by a surgeon. Alternatively, other planes also can be used as the projection planes and can span the reference coordinate system R.

Figure 8:
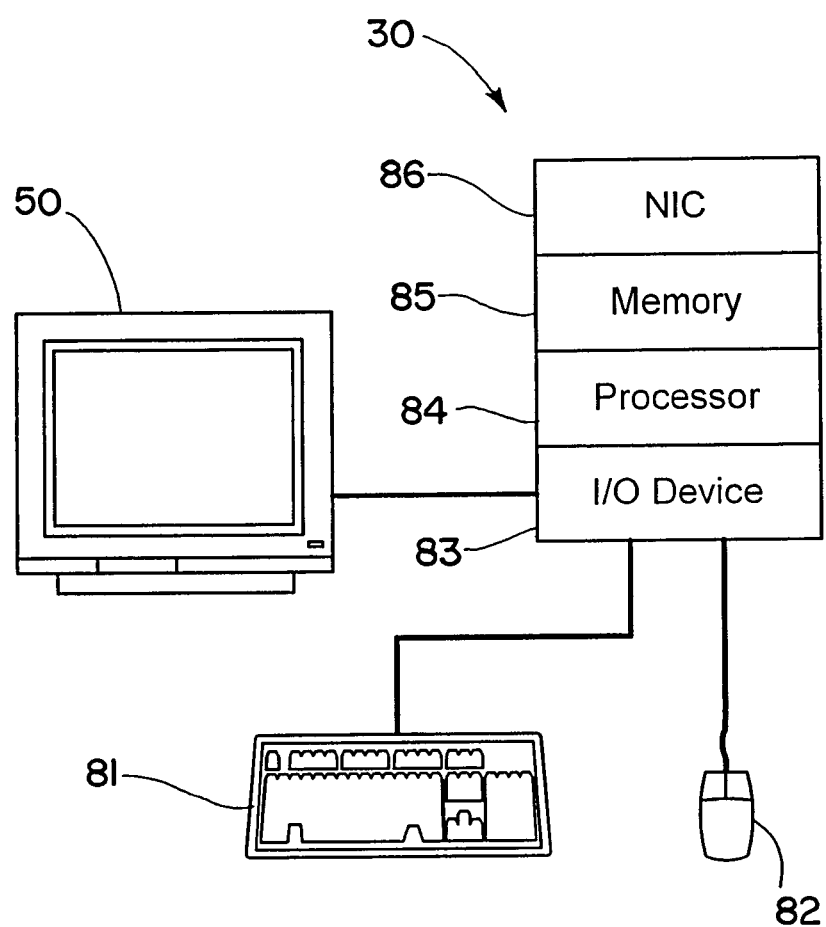
FIG. 8 illustrates a block diagram of an exemplary computer that may be used to implement one or more of the methods described herein.

Turning now to FIG. 8 there is shown a block diagram of an exemplary computer 30 that may be used to implement one or more of the methods described herein. The computer 30 may be a standalone computer, or it may be part of a medical navigation system 17, for example. The computer 30 may include a display or monitor 50 for viewing system information, and a keyboard 81 and pointing device 82 for data entry, screen navigation, etc. Examples of a pointing device 82 include a computer mouse or other device that points to or otherwise identifies a location, action, etc., e.g., by a point and click method or some other method. Alternatively, a touch screen (not shown) may be used in place of the keyboard 81 and pointing device 82. The display 50, keyboard 81 and mouse 82 communicate with a processor via an input/output device 83, such as a video card and/or serial port (e.g., a USB port or the like).

A processor 84, such as an AMD Athlon 64® processor or an Intel Pentium IV® processor, combined with a memory 85 execute programs to perform various functions, such as data entry, numerical calculations, screen display, system setup, etc. The memory 85 may comprise several devices, including volatile and non-volatile memory components. Accordingly, the memory 85 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 84 and the memory 85 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 86 allows the computer 30 to communicate with other devices. Such other devices a medical navigation system 17.

A person having ordinary skill in the art of computer programming and applications of programming for computer systems would be able in view of the description provided herein to program a computer system 30 to operate and to carry out the functions described herein. Accordingly, details as to the specific programming code have been omitted for the sake of brevity. Also, while software in the memory 85 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium, upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed Figures. In particular regard to the various functions performed by the above described elements (components, assemblies, devices, software, computer programs, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A cutting block for making an incision into a patient's bone, configured for use with a navigation system configured to define a reference coordinate system with respect to the patient's bone, the cutting block comprising:

a cutting guide having an incision plane;

a first localization reference trackable by the navigation system and attached to the cutting guide for determining a three-dimensional spatial position of the incision plane;

a fixation device configured to be fixable to the bone;

a pre-adjusting device including a second localization reference trackable by the navigation system, the pre-adjusting device having a first end coupled to the fixation device and a second movable end having a base coordinate system associated therewith and to which the second localization reference is attached, the pre-adjusting device adjustable for aligning the base coordinate system with respect to the reference coordinate system such that a first axis of the base coordinate system runs parallel to a plane spanned by two axes of the reference coordinate system, and a second axis of the base coordinate system runs parallel to a third axis of the reference coordinate system; and an adjusting device having a first end fixed in relation to the base coordinate system and a second end adjustable relative to the first end of the adjusting device, wherein the adjusting device is operative to set a position of the incision plane relative to the bone with two rotational degrees of freedom and one translational degree of freedom after alignment of the pre-adjusting device, the adjusting device.

2. The cutting block according to claim 1, wherein locations of reference objects of a body of the patient are defined with respect to the reference coordinate system, and wherein the reference objects comprise reference points, reference axes, reference straight lines, or reference planes.

3. The cutting block according to claim 1, wherein the pre-adjusting device further comprises pre-adjusting setting elements.

4. The cutting block according to claim 3, wherein the pre-adjusting setting elements comprise one setting element for each of two degrees of freedom of the cutting guide.

5. The cutting block according to claim 4, wherein the pre-adjusting setting elements comprise two hand wheel screw setting elements or locking screws for allowing the cutting guide to be rotated about two non-parallel axes.

6. The cutting block according to claim 1, wherein the pre-adjusting device is connectedly located between the fixation device and the adjusting device.

7. The cutting block according to claim 1, wherein the pre-adjusting device comprises a plurality of joints, about which the base coordinate system can be rotated.

* * * * *